US009238040B2

(12) United States Patent
Das et al.

(10) Patent No.: US 9,238,040 B2
(45) Date of Patent: Jan. 19, 2016

(54) CHEMOPREVENTION OF COLORECTAL CANCER BY MESALAMINE/SULFASALAZINE

(75) Inventors: Kiron M. Das, Basking Ridge, NJ (US); Jim Jung-Ching Lin, Iowa City, IA (US)

(73) Assignees: RUTGERS, THE STATE UNIVERSITY OF NEW JERSEY, New Brunswick, NJ (US); UNIVERSITY OF IOWA RESEARCH FOUNDATION, Iowa City, IA (US)

( * ) Notice: Subject to any disclaimer, the term of this patent is extended or adjusted under 35 U.S.C. 154(b) by 2527 days.

(21) Appl. No.: 11/914,849

(22) PCT Filed: May 17, 2006

(86) PCT No.: PCT/US2006/019225
§ 371 (c)(1),
(2), (4) Date: Jun. 19, 2008

(87) PCT Pub. No.: WO2006/125073
PCT Pub. Date: Nov. 23, 2006

(65) Prior Publication Data
US 2011/0059924 A1    Mar. 10, 2011

Related U.S. Application Data

(60) Provisional application No. 60/681,602, filed on May 17, 2005.

(51) Int. Cl.
A61K 31/655   (2006.01)
A61K 31/196   (2006.01)
A61P 35/00    (2006.01)
C07C 229/64   (2006.01)
A61K 31/695   (2006.01)
A61K 31/635   (2006.01)
C07K 14/47    (2006.01)

(52) U.S. Cl.
CPC ............. *A61K 31/695* (2013.01); *A61K 31/635* (2013.01); *A61K 31/655* (2013.01); *C07K 14/4713* (2013.01); *C07K 14/4716* (2013.01)

(58) Field of Classification Search
CPC . A61K 31/635; A61K 31/695; A61K 31/655; C07K 14/4716; C07K 14/4713
See application file for complete search history.

(56) References Cited

U.S. PATENT DOCUMENTS 5,905,073 A * 5/1999 Johnson et al. ............... 514/150

FOREIGN PATENT DOCUMENTS

WO   03/007890   1/2003

OTHER PUBLICATIONS

Anderson (Chem and Biol 10:787-797, 2003.*
(Continued)

*Primary Examiner* — Savitha Rao
(74) *Attorney, Agent, or Firm* — Fox Rothschild LLP

(57) ABSTRACT

A method for preventing colorectal cancer in a patient possessing human tropomyocin isoform TC22 is disclosed. The method comprises: (a) detecting a serum protein concentration of TC22 in a patient and (b) administering to said patient prior to detecting colorectal cancer in said patient a therapeutically effective amount of a chemotherapeutic composition comprising a chemotherapeutic compound that reduces the level of TC22, wherein the chemotherapeutic compound is selected from the group consisting of sulfasalazine, 5-amino-2-hydroxybenzoic acid, osalazine, and balsalazide.

4 Claims, 11 Drawing Sheets

(56) References Cited

OTHER PUBLICATIONS

Thiel (Nature Biotechnol 2:513-519, 2004.*
Hawk et al. (Journal of clinical oncology, 2005, vol. 23 (2), pp. 378-391.*
Croog (Int J Colorectal Disease, 2003, vol. 18, pp. 392-400.*
Lin et al. (Gastroenterology, 2002, vol. 123(1) pp. 152-162, abstract.*
Author Unknown, New Drug Evaluation: Balsalazide, Regional Drug and Therapeutics Centre, Jan. 1998, No. 13, printed p. 1 and 2.

* cited by examiner

Figure 4a.

```
   1 ggtgggcac catggctggg atcaccacca tcgaggcggt gaagcgcaag atccaggttc
  61 tgcagcagca ggcagatgat gcagaggagc gagctgaggc cctccagcga gaagctgagg
 121 gagaaaggcg ggccccggaa caggctgagg ctgaggtggc ctcccttgaac cgtaggatcc
 181 agctggttga agaagagctg gaccgtgctc aggagcgcct ggccactgcc ctgcaaaagc
 241 tggaagaagc agaaaaagct gctgatgaga gtgagagagg tatgaaggtt attgaaaacc
 301 gggcctaaa agatgaagaa aagatgaaat ccaactcaaa gaagctaagc
 361 acattgcaga agaggcagat aggaggtggc tgtaagttg gtgatcattg
 421 aaggagactt ggaacgcaca gaggaacgag ctgacctggc agagtcccgt gccgagagga
 481 tggatgagca gattagactg atggaccaga acctgaagtg tctgagtgct gctgaagaaa
 541 agtactctca aaagaagat aaatatgagg aagaaaatcaa gatcctact gataaactca
 601 aggagactga gagccgtgct gagttggctg agagatcggt agccaagctg cttctaatg
 661 ctgatgacct ggaagagcgt ctctacagcc acttgagcg agagatcggc aaaccgcccg gatgccatt
 721 agctgaagct aacgctgcat gatctgtgttg actgatggc aggctcaat tcattcctaa attgcctttt
 781 aaactgagct tactgctcac accactgacc tggacccccaa caaaaagctg ttgggcagt tagaatgctg
 841 tcaaagtcat tatttagcc ctgagcaaat tgcatttttaa tgtcctttt ctgtcctta gaagagatta
 901 attccctaac agcatgttga agttgaccat tgtgaagttt eactgcgag
 961 tggtgaga aggagtggc ctgagagatt atagtgegaa atagtgagaa taggatatgt aacctgtctt
1021 tccaccctta ttgctgtctc ttccacttgg gcactgactg taggatatgt tccctgcat
1081 ggactgactt aacaataaaa ggactgactt gaaaaaaaaa aaaaaaaaa a
```

Figure 4b.

```
  1 magittieav krkiqvlqqg addaeeraer lqrevegecr aregaeaeva slnrriglve
 61 eeldrageri atalgkleea ekaadjeserg mkvienralk daeekmelgei glkeakhiae
121 eadrkyseva rklviiegdl erteeraela esrcremdeg irlmdqnikc lsaaeekysq
181 kedkyeeeik iltdklkeae traefaeersv aklektiddl aerlyadler nklisneiki
241 tlhdlcd
```

CHEMOPREVENTION OF COLORECTAL CANCER BY MESALAMINE/SULFASALAZINE

CROSS REFERENCE TO RELATED APPLICATIONS

This application is a National Stage of International Application No. PCT/US2006/019225, filed May. 17, 2006, which claims priority under 35 U.S.C. 119(e) to U.S. Provisional Application Ser. No. 60/681,602, which was filed on May. 17, 2005. The disclosures of both are incorporated herein by reference.

INCORPORATION OF SEQUENCE LISTING

A computer readable form of the Sequence Listing, named P32,303A_USA_Sequence_Listing.txt, created on Jun. 19, 2008, and 3,984 bytes in size, is herein incorporated by reference.

BACKGROUND OF THE INVENTION

Colorectal cancer, or cancer of the colon and rectum, is the second leading cause of cancer-related deaths in the United States, and the third most common cancer overall. The American Cancer Society estimates that each year more than 50,000 Americans die from colorectal cancer and approximately 155,000 new cases are diagnosed, accounting for 15% of all types of tumor. Eighty to 90 million Americans (approximately 25% of the U.S. population) are considered at risk because of age or other factors. More women over the age of 75 die from colorectal cancer than from breast cancer. The 5-year survival rate remains at approximately 45%.

The exact causes of colorectal cancer are unknown, but the disease appears to be caused by both inherited and lifestyle factors. Known predisposing conditions for colorectal cancer include familial adenomatous polyposis (FAP), hereditary nonpolyposis colon cancer (HNPCC), Lynch I Syndrome, Lynch II Syndrome, family cancer syndromes, adenomatous polyps (sessile or tubular), and inflammatory bowel disease, including both chronic ulcerative colitis (UC) and Crohn's disease.

Autoimmunity has been emphasized in the pathogenesis of UC. Autoimmune responses (both humoral and cellular) against human tropomyosin (TM) isoform 5 (hTM5) in UC have been reported (Gastroenterology 114:912, 1998, Clinical Immunology 101:289, 2001). hTM 5 is the predominant TM in colon epithelial cells and is expressed on the colon epithelial cell surface which may be critical for autoimmune effector response.

WO 03/007890, the contents of which are incorporated herein by reference in their entirety, discloses a novel hTM isoform, TC22. TC22 is strongly associated with colonic neoplasia and carcinoma (with almost 100% sensitivity) but is not detected in normal colon epithelium (Gastroenterology 123:152, 2002). TC22 is identical to hTM5 apart from the C-terminal domain. Recently, a pilot study of non-dysplastic, colonic tissues from UC and normal subjects showed that TC22 expression was associated with UC complicated with primary sclerosing cholangitis and long standing pancolitis—the two conditions known to be strongly associated with colon cancer in UC (Xin, Jeng et al., "Expression of a Novel Biomarker in Colonic Mucosa of Patients with Ulcerative Colitis At High Risk For Colon Cancer," Gastroenterology vol. 126, T1229 (2004)).

U.S. Pat. Nos. 5,498,608 and 5,905,073 disclose the use of 2-hydroxy-5-phenylazobenzoic acid derivatives as colon cancer chemopreventive and chemotherapeutic agents. However, the mechanism by which these chemotherapeutic agents operate is not entirely understood.

SUMMARY OF THE INVENTION

The present invention provides a method for preventing or treating colorectal cancer in a patient including: (a) detecting a serum protein concentration of TC22 in a patient and (b) administering to the patient a therapeutically effective amount of a chemotherapeutic composition comprising a chemotherapeutic compound that reduces the level of TC22.

Also presented is a method for preventing or treating colorectal cancer in a patient including: (a) detecting a serum protein concentration of TC22 in a patient and (b) administering to the patient a therapeutically effective amount of a chemotherapeutic composition.

Another embodiment provides a method for evaluating TC22 expression reduction activity of a compound including exposing LS180 colon cancer cells to the compound and measuring TC22 expression level.

Yet another embodiment provides the use of a compound of formula I in the manufacture of a medicament for preventing or treating colon cancer in a patient possessing human tropomyocin isoform TC22.

BRIEF DESCRIPTION OF THE DRAWINGS

FIG. 4a is the full length mRNA of the Tropomyosin TC22 as set forth in Genbank at Accession No. AY004867 (SEQ ID NO 1);
and
FIG. 4b is the corresponding full-length translated protein of FIG. 4a as set forth in Genbank at Accession No. AAF87083 (SEQ ID NO 2).

DETAILED DESCRIPTION OF THE INVENTION

Figure 1A:
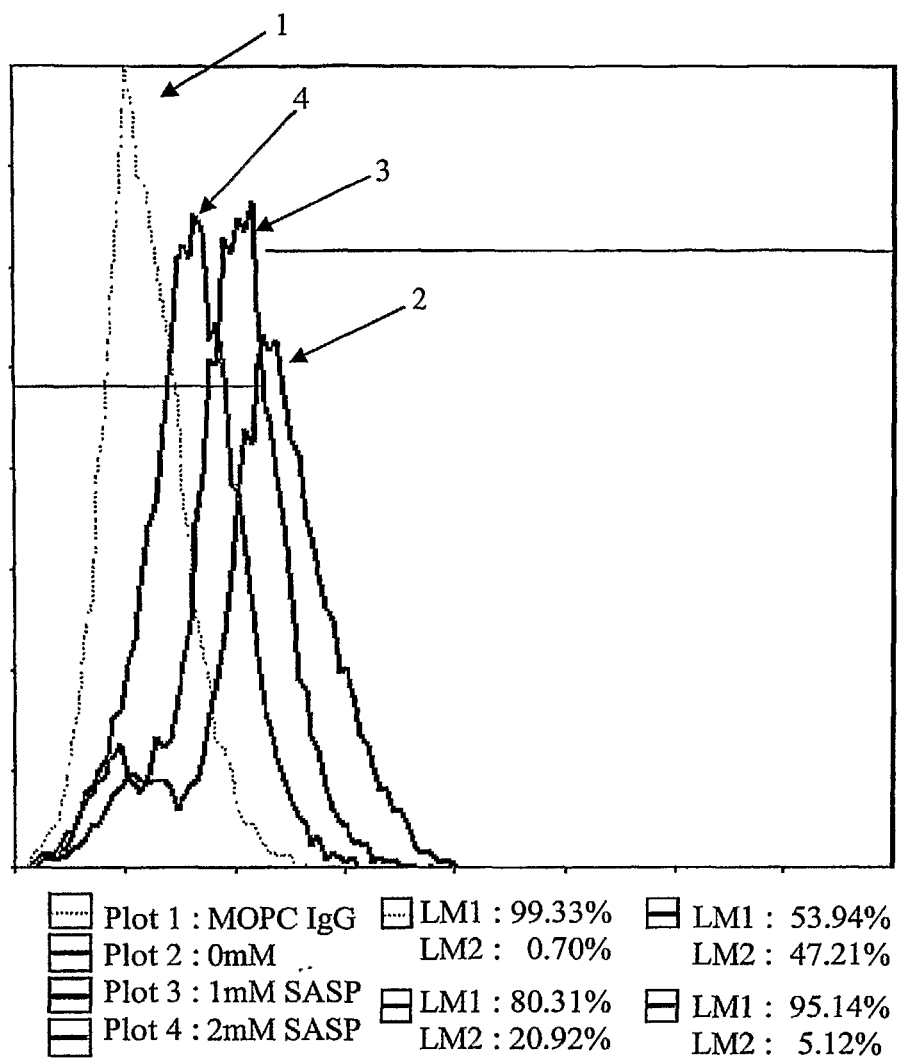
FIG. 1a is an FACS plot at 4 hours with SASP.
Figure 1B:
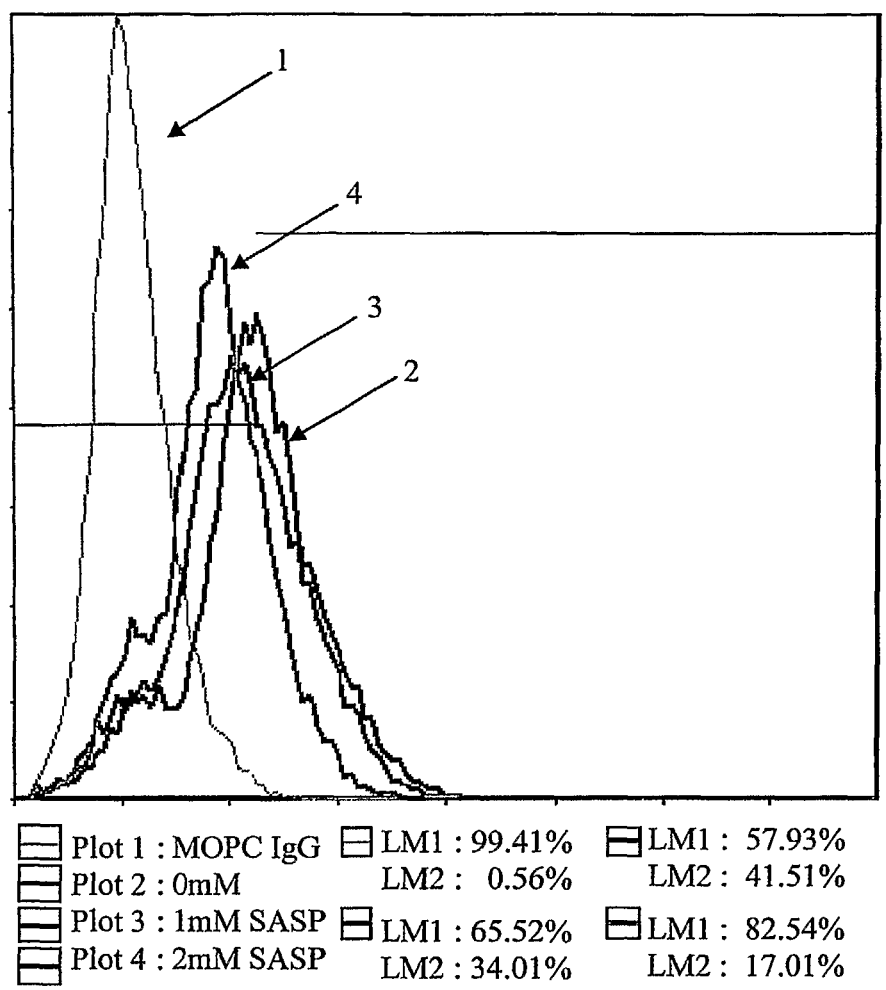
FIG. 1b is an FACS plot at 24 hours with SASP.
Figure 1C:
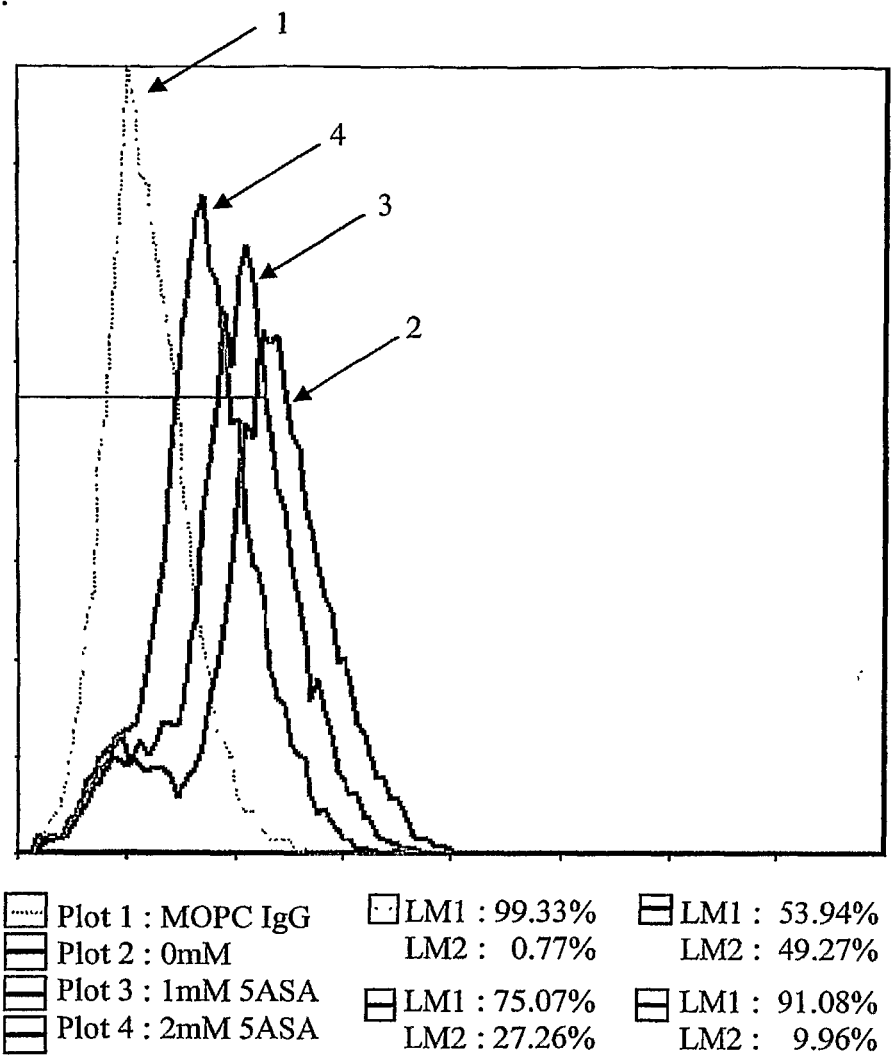
FIG. 1c is an FACS plot at 4 hours with 5-ASA.
Figure 1D:
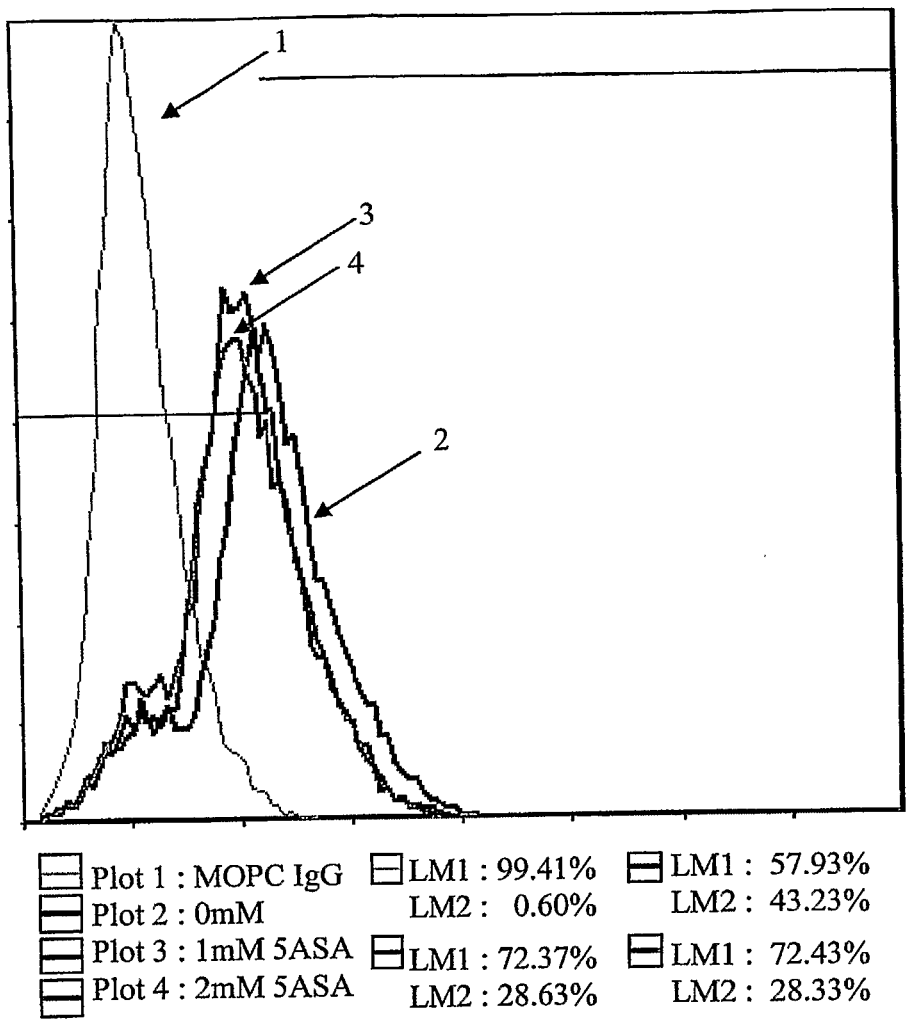
FIG. 1d is an FACS plot at 24 hours with 5-ASA.

The present invention incorporates the discovery of a novel human tropomyocin (TM) isoform, TC22, the expression of which is strongly associated with colonic neoplasia and carcinoma (with almost 100% sensitivity). This suggests that TC22 expression may be an important biomarker to identify patients at high risk for colon carcinogenesis.

Therefore, according to one aspect of the present invention, a method for preventing or treating colorectal cancer in a patient comprising: (a) detecting a serum protein concentration of TC22 in a patient and (b) administering to said patient a therapeutically effective amount of a composition comprising a compound that reduces the level of TC22. The present invention includes TC22, analogs, mimics, variants, and fragments thereof, including such materials as are immunogenic. In a preferred embodiment, the therapeutic compound has a structure according to formula I:

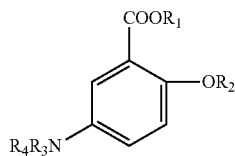

wherein

R$_1$ is an acid-protecting group, such as, for example, hydrogen;
- (C$_{1-6}$)alkyl optionally substituted by at least one substituent independently selected from halo, cyano, nitro, (C$_{1-6}$)alkyl, halogenated (C$_{1-6}$)alkyl, (C$_{1-6}$)alkanoyl, (C$_{1-6}$)alkoxy, (C$_{1-6}$)alkoxycarbonyl, (C$_{1-6}$)alkylamino, —(CH$_2$)$_r$—COOR$^{b1}$, —(CH$_2$)$_r$—CONR$^{b1}$R$^{b2}$, —(CH$_2$)$_r$—NR$^{b1}$R$^{b2}$, —(CH$_2$)$_r$—NR$^{b1}$—COR$^{b2}$, —(CH$_2$)$_r$—NHSO$_2$R$^{b1}$, —(C$_2$)$_r$—OR$^{b1}$, —(CH$_2$)$_r$—SR$^{b1}$, —(CH$_2$)$_r$—SO$_2$R$^{b1}$, and —(CH$_2$)$_r$—SO$_2$NR$^{b1}$R$^{b2}$, wherein R$^{b1}$ and R$^{b2}$ are each independently hydrogen or (C$_{1-6}$)alkyl and r is 0 to 6; (C$_{1-6}$) alkylaryl; benzyl; and silyl;

R$_2$ is hydrogen;
- (C$_{1-6}$)alkyl optionally substituted by at least one substituent independently selected from the group consisting of halo, cyano, nitro, (C$_{1-6}$)alkyl, halogenated (C$_{1-6}$)alkyl, (C$_{1-6}$)alkanoyl, (C$_{1-6}$)alkoxy, (C$_{1-6}$)alkoxycarbonyl, (C$_{1-6}$)alkylamino, —(CH$_2$)$_r$—COOR$^{b1}$, —(CH$_2$)$_r$—CONR$^{b1}$R$^{b2}$, —(CH$_2$)$_r$—NR$^{b1}$R$^{b2}$, —(CH$_2$)$_r$—NR$^{b1}$—COR$^{b2}$, —(CH$_2$)$_r$—NHSO$_2$R$^{b1}$, —(CH$_2$)$_r$—OR$^{b1}$, —(CH$_2$)$_r$—SR$^{b1}$, —(CH$_2$)$_r$—SO$_2$R$^{b1}$ and —(CH$_2$)$_r$—SO$_2$NR$^{b1}$R$^{b2}$, wherein R$^{b1}$ and R$^{b2}$ are each independently hydrogen or (C$_{1-6}$)alkyl and r is 0 to 6; or
- Si(R$_{a-c}$)$_3$, wherein R$_{a-c}$ are each independently selected from the group consisting of
  - (C$_{1-6}$)alkyl optionally substituted by at least one substituent independently selected from the group consisting of halo, cyano, nitro, (C$_{1-6}$)alkyl, halogenated (C$_{1-6}$)alkyl, (C$_{1-6}$)alkanoyl, (C$_{1-6}$)alkoxy, (C$_{1-6}$) alkoxycarbonyl, (C$_{1-6}$)alkylamino, —(CH$_2$)$_r$—COOR$^{b1}$, —(CH$_2$)$_r$—CONR$^{b1}$R$^{b2}$, —(CH$_2$)$_r$—NR$^{b1}$R$^{b2}$, —(CH$_2$)$_r$—NR$^{b1}$—COR$^{b2}$, —(CH$_2$)$_r$—NHSO$_2$R$^{b1}$, —(CH$_2$)$_r$—SR$^{b1}$, —(CH$_2$)$_r$—SO$_2$R$^{b1}$ and —(CH$_2$)$_r$—SO$_2$NR$^{b1}$R$^{b2}$, wherein R$^{b1}$ and R$^{b2}$ are each independently hydrogen or (C$_{1-6}$)alkyl and r is 0 to 6; and
  - phenyl optionally substituted by at least one substituent independently selected from the group consisting of halo, cyano, nitro, (C$_{1-6}$)alkyl, halogenated (C$_{1-6}$) alkyl, (C$_{1-6}$)alkanoyl, (C$_{1-6}$)alkoxy, (C$_{1-6}$)alkoxycarbonyl, (C$_{1-6}$)alkylamino, —(CH$_2$)$_r$COOR$^{b1}$, —(CH$_2$)$_r$—CONR$^{b1}$R$^{b2}$, —(CH$_2$)$_r$—NR$^{b1}$R$^{b2}$, —(CH$_2$)$_r$—NR$^{b1}$—COR$^{b2}$, —(CH$_2$)$_r$—NHSO$_2$R$^{b1}$, —(CH$_2$)$_r$—OR$^{b1}$, —(CH$_2$)$_r$—SR$^{b1}$, —(CH$_2$)$_r$—SO$_2$R$^{b1}$, and —(CH$_2$)$_r$—SO$_2$NR$^{b1}$R$^{b2}$, wherein R$^{b1}$ and R$^{b2}$ are each independently hydrogen or (C$_{1-6}$) alkyl and r is 0 to 6; and R$_3$ and R$_4$ are independently hydrogen, (C$_{1-6}$)alkyl, C(=O)(C$_{1-6}$)alkyl, C(C=O)O(C$_{1-6}$)alkyl, or R$_3$ and R$_4$ together form an R$_5$N= group with the nitrogen to which they are attached, wherein R$_5$ is a phenyl group optionally substituted by at least one substituent independently selected from the group consisting of:
halo, cyano, nitro, (C$_{1-6}$)alkyl, halogenated (C$_{1-6}$)alkyl, (C$_{1-6}$)alkanoyl, (C$_{1-6}$)alkoxy, (C$_{1-6}$)alkoxycarbonyl, (C$_{1-6}$) alkylamino, —(CH$_2$)$_r$—COOR$^{b1}$, —(CH$_2$)$_r$—CONR$^{b1}$R$^{b2}$, —(CH$_2$)$_r$—NR$^{b1}$R$^{b2}$, —(CH$_2$)$_r$—NR$^{b1}$—COR$^{b2}$, —(CH$_2$)$_r$—NHSO$_2$R$^{b1}$, —(CH$_2$)$_r$—OR$^{b1}$, —(CH$_2$)$_r$—SR$^{b1}$, —(CH$_2$)$_r$—SO$_2$R$^{b1}$, —(CH$_2$)$_r$—SO$_2$NR$^{b1}$R$^{b2}$, wherein R$^{b1}$ and R$^{b2}$ are each independently hydrogen or (C$_{1-6}$)alkyl and r is 0 to 6; and —X—NH—R$_6$, wherein X is —SO$_2$— or —CO—; and R$_6$ is either a phenyl, a pyridyl, or carboxymethylphenyl radical or is a radical of the formula —(CH$_2$)$_n$—Y, in which Y is a hydroxyl group, an amino group, a monoalkyl- or dialkyl-amino group, the alkyl moieties of which contain up to 6 carbon atoms or a carboxylic or sulphonic acid group, and n is a whole number of from 1 to 6, and in which one or more of the hydrogen atoms in the alkylene radical can be replaced by amino groups, monoalkyl- or dialkyl-amino groups, the alkyl moieties of which contain up to 6 carbon atoms or alkyl radicals, and in which the —(CH$_2$)$_n$—Y radical is either attached directly to the nitrogen atom or via a benzene ring;

or a derivative of said compound selected from the group consisting of N-oxide derivatives, prodrug derivatives, protected derivatives, isomers, and mixtures of isomers of said compound; or a pharmaceutically acceptable salt or solvate of said compound or said derivative.

Analogs of the compound of formula I, which reduce or result in the reduced expression of TC22, are also suitable for use in the present invention.

The term "analog" relates to any compound which is derived from a compound that reduces or results in the reduction of the expression of TC22 and which substantially maintains the activity of the compound from which it was derived.

In a preferred embodiment, the compound of formula I is selected from:

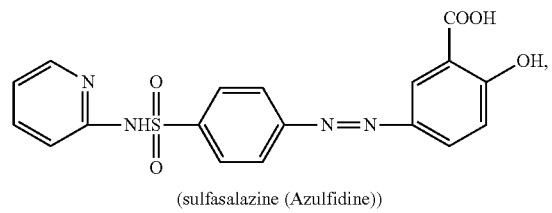

(sulfasalazine (Azulfidine))

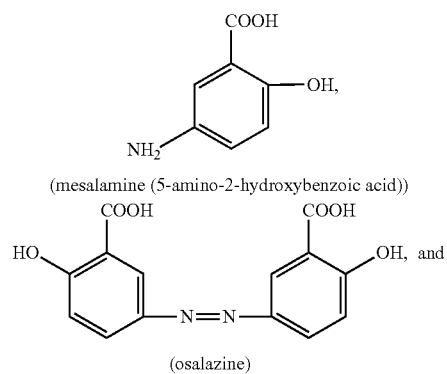

(mesalamine (5-amino-2-hydroxybenzoic acid))

(osalazine)

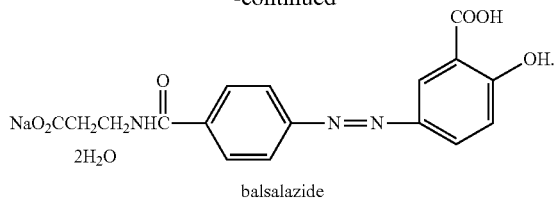

balsalazide

One embodiment includes administering a compound that reduces the expression of TC22 prior to detecting colorectal cancer in a patient or after detecting colorectal cancer in a patient.

In another embodiment, the method includes administering the compound to a patient suffering from ulcerative colitis complicated with primary sclerosing cholangitis or long standing pancolitis.

Another embodiment further includes discontinuing the administration of the chemotherapeutic composition when TC22 is no longer detectable in the patient's blood stream.

One embodiment includes a method for preventing or treating colorectal cancer in a patient comprising: (a) detecting a serum protein concentration of TC22 in a patient and (b) administering to the patient a therapeutically effective amount of a chemotherapeutic composition.

In another embodiment, the composition further includes a pharmaceutically acceptable carrier.

The term "effective amount" or "therapeutically effective amount" means that amount of a compound or agent that will elicit the biological or medical response of a subject that is being sought by a medical doctor or other clinician.

In practice, the chemotherapeutic composition may be administered in any variety of suitable forms, for example, topically, parenterally, rectally, or orally. More specific routes of administration include intravenous, intramuscular, subcutaneous, intraocular, intrasynovial, colonical, peritoneal, transepithelial including transdermal, ophthalmic, sublingual, buccal, dermal, ocular, nasal inhalation via insufflation, and aerosol.

The chemotherapeutic composition may be presented in forms permitting administration by the most suitable route. The invention also relates to administering compositions containing a compound that reduces the expression of TC22 which is suitable for use as a medicament in a patient. These compositions may be prepared according to the customary methods, using one or more pharmaceutically acceptable adjuvants or excipients. The adjuvants comprise, inter alia, diluents, sterile aqueous media and the various non-toxic organic solvents. The compositions may be presented in the form of oral dosage forms, or injectable solutions, or suspensions.

The choice of vehicle and the chemotherapeutic compound that reduces the expression of TC22 in the vehicle are generally determined in accordance with the solubility and chemical properties of the product, the particular mode of administration and the provisions to be observed in pharmaceutical practice. When aqueous suspensions are used they may contain emulsifying agents or agents which facilitate suspension. Diluents such as sucrose, ethanol, polyols such as polyethylene glycol, propylene glycol and glycerol, and chloroform or mixtures thereof may also be used. In addition, the chemotherapeutic compound that reduces the expression of TC22 may be incorporated into sustained-release preparations and formulations.

For parenteral administration, emulsions, suspensions or solutions of the compounds according to the invention in vegetable oil, for example sesame oil, groundnut oil or olive oil, or aqueous-organic solutions such as water and propylene glycol, injectable organic esters such as ethyl oleate, as well as sterile aqueous solutions of the pharmaceutically acceptable salts, are used. The injectable forms must be fluid to the extent that it can be easily syringed, and proper fluidity can be maintained, for example, by the use of a coating such as lecithin, by the maintenance of the required particle size in the case of dispersion and by the use of surfactants. Prolonged absorption of the injectable compositions can be brought about by use of agents delaying absorption, for example, aluminum monostearate and gelatin. The solutions of the salts of the products according to the invention are especially useful for administration by intramuscular or subcutaneous injection. Solutions of the compound that reduces the expression of TC22 as a free base or pharmacologically acceptable salt can be prepared in water suitably mixed with a surfactant such as hydroxypropyl-cellulose. Dispersion can also be prepared in glycerol, liquid polyethylene glycols, and mixtures thereof and in oils. The aqueous solutions, also comprising solutions of the salts in pure distilled water, may be used for intravenous administration with the proviso that their pH is suitably adjusted, that they are judiciously buffered and rendered isotonic with a sufficient quantity of glucose or sodium chloride and that they are sterilized by heating, irradiation, microfiltration, and/or by various antibacterial and antifungal agents, for example, parabens, chlorobutanol, phenol, sorbic acid, thimerosal, and the like.

Sterile injectable solutions are prepared by incorporating the compound that reduces the expression of TC22 in the required amount in the appropriate solvent with various of the other ingredients enumerated above, as required, followed by filtered sterilization. Generally, dispersions are prepared by incorporating the various sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the freeze drying technique, which yield a powder of the active ingredient plus any additional desired ingredient from previously sterile-filtered solution thereof.

Topical administration, gels (water or alcohol based), creams or ointments containing the chemotherapeutic compound that reduces the expression of TC22 may be used. The compound that reduces the expression of TC22 may be also incorporated in a gel or matrix base for application in a patch, which would allow a controlled release of compound through transdermal barrier.

The percentage of the chemotherapeutic compound that reduces the expression of TC22 in the chemotherapeutic compositions used in the present invention may be varied, it being necessary that it should constitute a proportion such that a suitable dosage shall be obtained. Obviously, several unit dosage forms may be administered at about the same time. A dose employed may be determined by a physician or qualified medical professional, and depends upon the desired therapeutic effect, the route of administration and the duration of the treatment, and the condition of the patient. In the adult, the doses are generally from about 0.001 to about 50, preferably about 0.001 to about 5, mg/kg body weight per day by inhalation, from about 0.01 to about 100, preferably 0.1 to 70, more especially 0.5 to 10, mg/kg body weight per day by oral administration, and from about 0.001 to about 10, preferably 0.01 to 10, mg/kg body weight per day by intravenous administration. In each particular case, the doses are determined in accordance with the factors distinctive to the patient to be treated, such as age, weight, general state of health and other characteristics, which can influence the efficacy of the compound according to the invention.

The compound that reduces the expression of TC22 used in the invention may be administered as frequently as necessary in order to obtain the desired therapeutic effect. Some patients may respond rapidly to a higher or lower dose and may find much weaker maintenance doses adequate. For other patients, it may be necessary to have long-term treatments at the rate of 1 to 4 doses per day, in accordance with the physiological requirements of each particular patient. Generally, the compound that reduces the expression of TC22 may be administered 1 to 4 times per day. Of course, for other patients, it will be necessary to prescribe not more than one or two doses per day.

Also presented is a method for evaluating TC22 expression reduction activity of a compound comprising exposing LS180 colon cancer cells to the compound and measuring TC22 expression level.

The following non-limiting examples set forth hereinbelow illustrate certain aspects of the invention.

EXAMPLES

The influence of sulfasalazine (SASP) and its two moieties 5-Aminosalicylic Acid (5-ASA) and sulfapyradine (SP) on the cellular expression of hTM5 and TC22 in-vitro utilizing LS180 colon cancer cells was examined. Specific monoclonal antibodies, CG3 for hTM5 and TC22-4 for TC22 were used against the cells in a fluorescent activated cell sorter (FACS). Reverse transcriptase PCR (RT-PCR) was utilized to quantify the transcription of hTM5 and TC-22.

Example 1

Fluorescent Activated Cell Sorter (FACS)

LS180 colon cancer cells were incubated with 0, 1 mM, and 2 mM of 5-ASA, SASP, and SP in Serum Free Media (SFM) for 2 hrs, 4 hrs, and 24 hrs. Dishes were washed with 10 ml PBS 3 times. Cells were detached with 0.25% trypsin-EDTA and collected. All cells were >90% viable.

The cells were washed and then fixed by using 4% paraformaldehyde for 5 minutes. Cells were washed 2 times. Cells were then resuspended and the first antibody was added: MOPC IgM(0.5 mg/mL) 1 µl (1:100), MOPCIgG(0.5 mg/mL) 1 µl (1:100), CG3 IgM(2.4 mg/mL) 1 µL of (2+3 µL Buffer) (1:250) for hTM5, TC22-4 IgG(30 mg/mL) 1 µL of (1+9 uL Buffer) (1:1000) for TC22. The suspension was incubated at 4° C. for 30 minutes, shaken and washed (2 times) with 30 vol. of PBS/0.5 BSA/2 mm EDTA.

The second antibody was added: 1 µl tube (1:100) Cy2 (Cyanine)-conj. G-α-M IgM or Cy2 (Cyanine)-conj. G-α-M IgM, then incubated at 4° C. for 30 minutes, shaken and washed (2 times) with 100 vol. buffer 2 times. The cells were then resuspended in 1 ml wash buffer. FACS was used to detect hTM5 and TC22 expression within 1 hour.

FIGS. 1a-d are FACS plots showing the effects of SASP and 5-ASA at different concentrations and time periods. The graphs show the number of cells as a function of fluorescence intensity. LM1 represents the percent of cells present but not expressing TC22. LM2 represents the percent of cells containing TC22.

Example 2

Reverse Transcriptase PCR(RT-PCR)

The expression levels of TC22 and hTM5 genes in LS180 cells were measured using semi quantitative RT-PCR (Perkin Elmer Gene Amp PCR system 9700). RNA was isolated from cells using RNeasy micro kit (Qiagen Inc.). RNA was eluted in a final volume of 18 ul. 11 µl of RNA was converted to first strand cDNA by reverse transcriptase in a 20 µl reaction using random hexamers and MLV reverse transcriptase (Invitrogen Inc, California). PCR reactions were carried out in 50 µl for 35 cycles using Taq polymerase (Invitrogen Inc, Carlsbad, Calif.). 4 µl of first strand cDNA was used to amplify TC22 gene, whereas 1 µl was used to amplify 18S RNA as a control. 18 µl of PCR products were analyzed on 1.5% agarose gel. The amount of PCR product for each sample was compared with that for 18S. The ratio of intensity for TC22 or hTM5 gene to that of 18S was quantified using Kodak EDAS290 gel documentation system. This ratio was used as a measure of the relative expression of TC22 and hTM5 gene before and after treating the cells with 5-ASA.

Figure 1E:
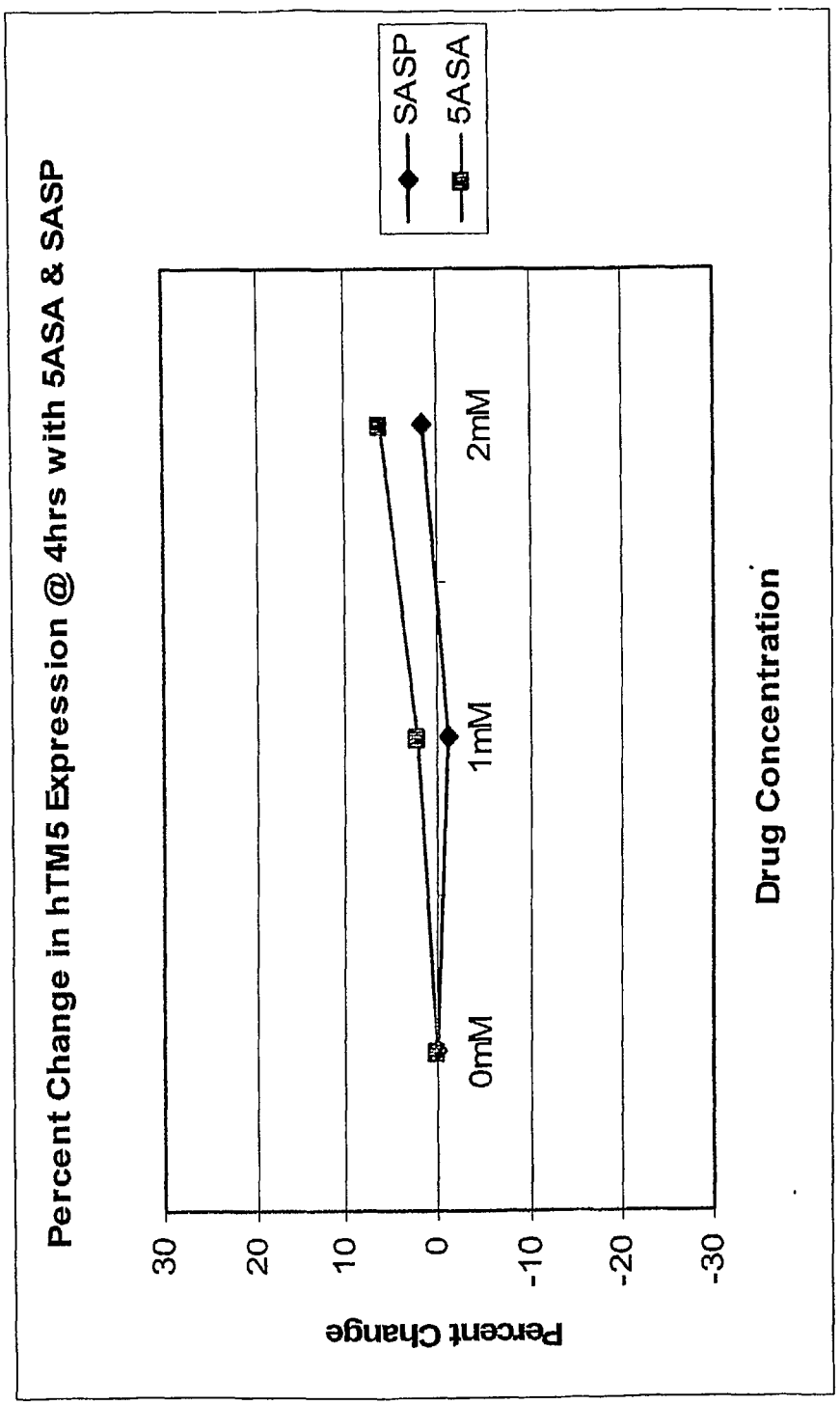
FIG. 1e is a graph illustrating the percent change in hTM5 expression at 4 hours with 5-ASA and SASP.
Figure 1F:
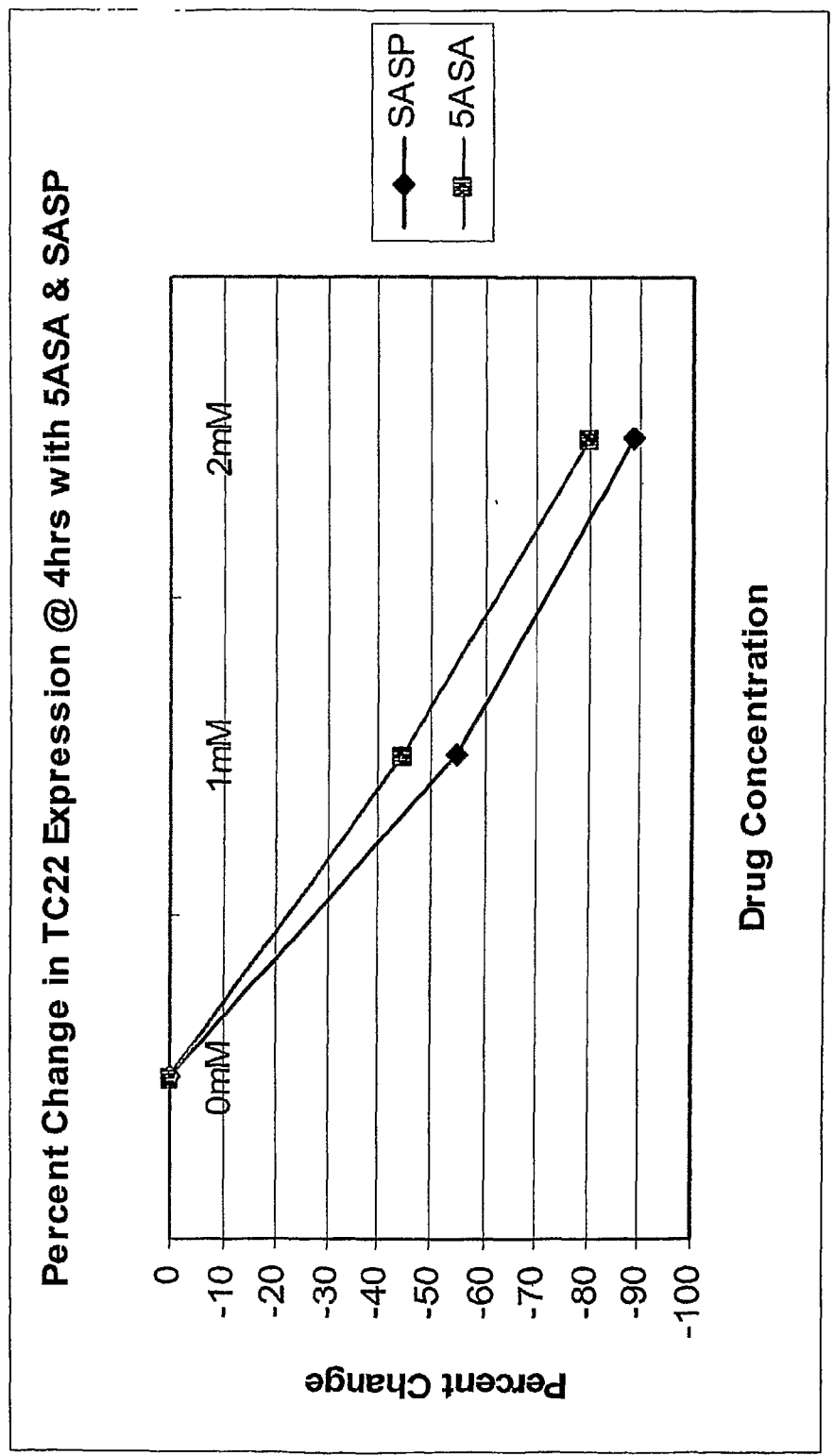
FIG. 1f is a graph illustrating the percent change in TC22 expression at 4 hours with 5-ASA and SASP.
Figure 2:
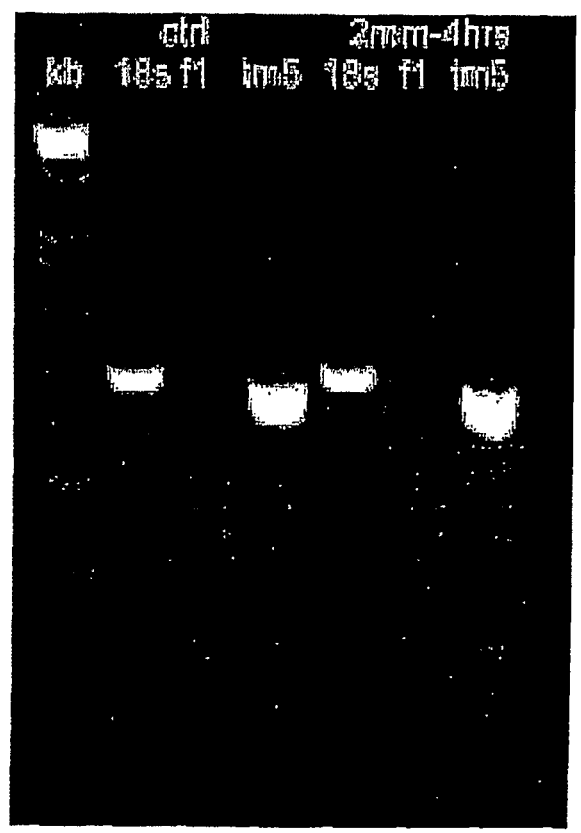
FIG. 2 is an agarose gel electrophoresis analysis of PCR products for 18s RNA, TC22 (fl), and hTM5, before and after treatment.
Figure 3A:
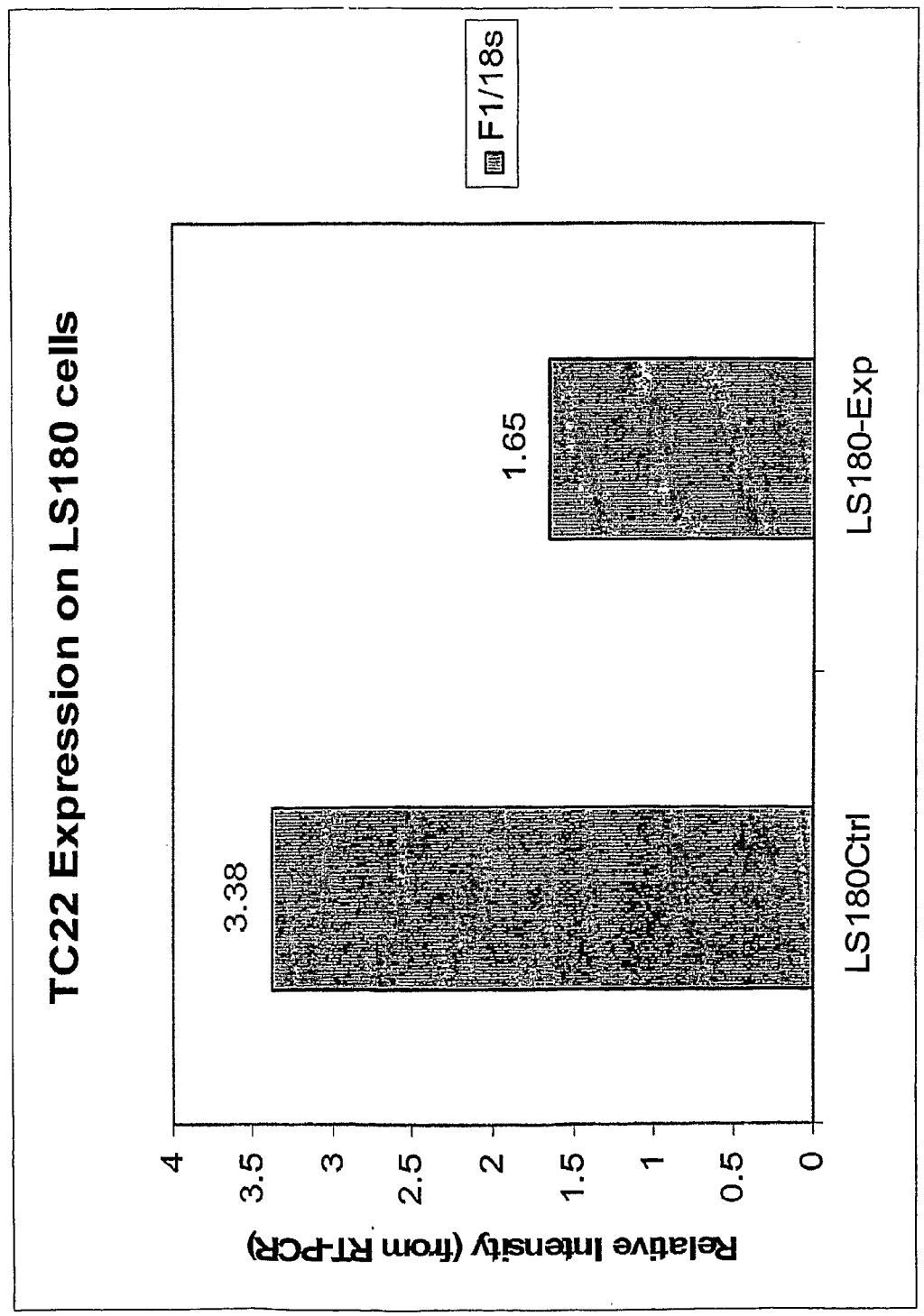
FIG. 3a is a graphic representation of the levels of TC22 estimated from the agarose gel.
Figure 3B:
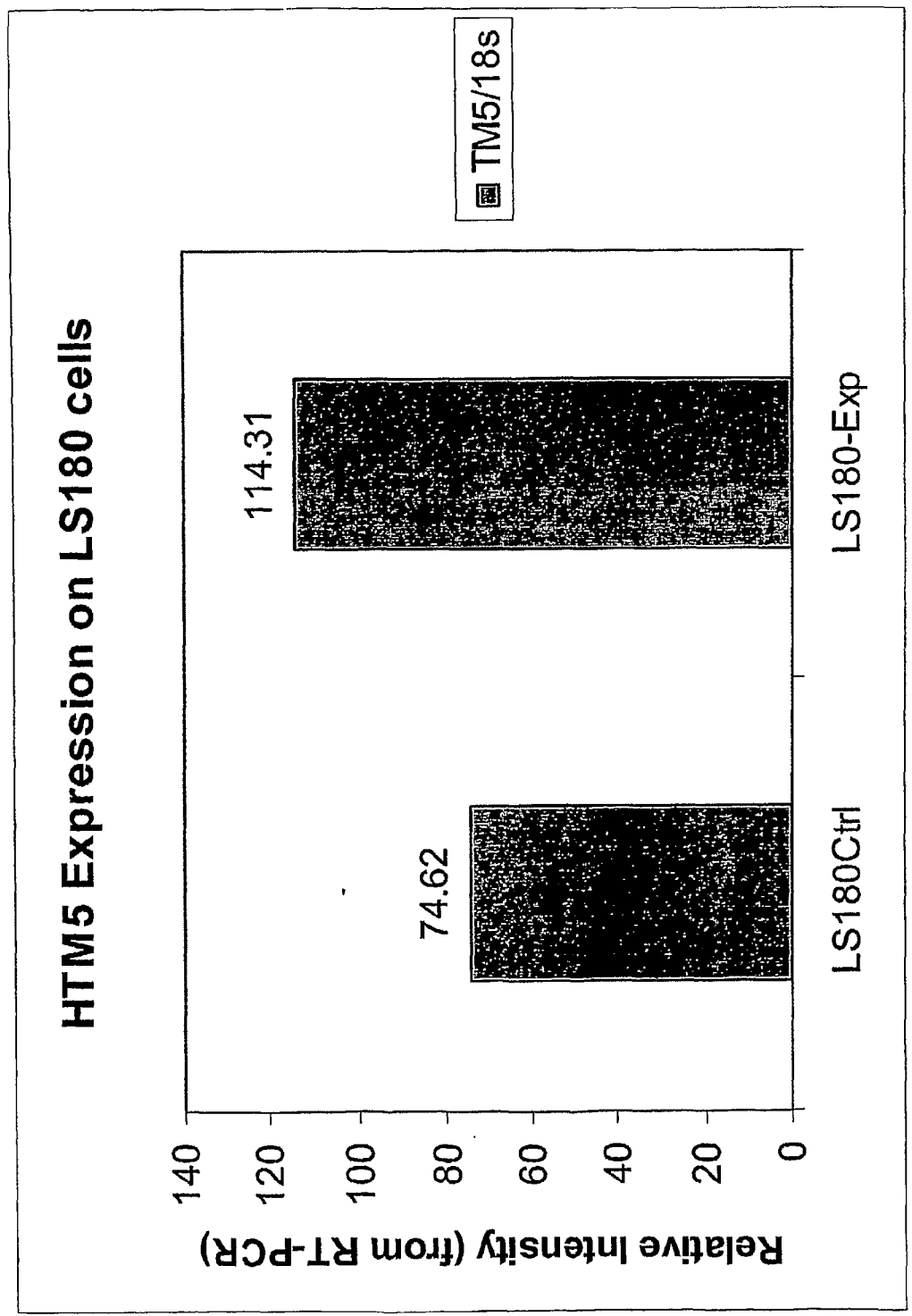
FIG. 3b is a graphic representation of the levels of hTM5 estimated from the agarose gel.

5-ASA reduced the expression of TC22 (FIGS. 1f and 3a), but not hTM5 (FIGS. 1e and 3b).

Example 3

Microarray Analysis

The initial single microarray analysis following exposure of LS180 cells with 200 mM of 5-ASA for 4 hours and 24 hours demonstrates both amplification and suppression of a number of genes when compared with the 5-ASA untreated LS180 cells, as shown in Table II:

TABLE II

| Changes in gene expression when compared with 5-ASA untreated cells | |
|---|---|
| Number of genes up-regulated: | >194 |
| Up-regulated by 2 logs: | CIRBP, PCK1, DEX28, LOC284926, LCMT2, ZNF214, PARS2, HSPC105, ZNF499, ZNF75A, CR8F9, BGL11, PHF17, MFG3, 1F1T2, AHSA2, TRIM59, ZNF529, C20orf18, OSGEPL1, ELAC1, 2NF13, PPAP2B, ZNF302, FLJ21125 |
| Number of genes down-regulated: | >385 |
| Down-regulated by 2 logs: | Family 1, MATF, ZBTB1, NR4A2, GEM, HSZFP36, BCL6, SERTAD1, SSL1D1, SPRY4, SUI1, PLK2 |

Up-regulated genes include various genes related to transcription, regulation of transcription, regulation of apoptosis, protein biosynthesis, zinc finger protein, immune response, heat shock activator protein, and 5 protein. Down-regulated genes include genes involved in transcription and regulation of transcription, immune response gene, negative regulation of transcription from RNA polymerase, protein biosynthesis, regulation of translational initiation, response to stress, and regulation of kappa B kinase/NF-kappa B cascade.

The foregoing examples and description of the preferred embodiments should be taken as illustrating, rather than as limiting the present invention as defined by the claims. As will be readily appreciated, numerous variations and combinations of the features set forth above can be utilized without departing from the present invention as set forth in the claims. Such variations are not regarded as a departure from the spirit and script of the invention, and all such variations are intended to be included within the scope of the following claims.

What is claimed is:

1. A method for preventing colorectal cancer in a patient comprising: (a) detecting a serum protein concentration of TC22 in a patient and (b) administering to said patient prior to detecting colorectal cancer in said patient a therapeutically effective amount of a chemotherapeutic composition comprising a chemotherapeutic compound that reduces the level of TC22, wherein the chemotherapeutic compound is selected from the group consisting of sulfasalazine, 5-amino-2-hydroxybenzoic acid, osalazine, and balsalazide.

2. The method of claim 1 wherein said composition further comprises a pharmaceutically acceptable carrier.

3. The method of claim 1 wherein said patient suffers from ulcerative colitis complicated with primary sclerosing cholangitis or long standing pancolitis.

4. The method of claim 1 further comprising discontinuing the administration of said chemotherapeutic composition when TC22 is no longer detectable in said patient's blood stream.

* * * * *

SEQUENCE LISTING

<160> NUMBER OF SEQ ID NOS: 2

<210> SEQ ID NO 1
<211> LENGTH: 1131
<212> TYPE: DNA
<213> ORGANISM: Homo sapiens

<400> SEQUENCE: 1

| | | | | | |
|---|---|---|---|---|---|
| gggtgggcac | catggctggg | atcaccacca | tcgaggcggt | gaagcgcaag | atccaggttc | 60 |
| tgcagcagca | ggcagatgat | gcagaggagc | gagctgagcg | cctccagcga | gaagttgagg | 120 |
| gagaaaggcg | ggcccgggaa | caggctgagg | ctgaggtggc | ctccttgaac | cgtaggatcc | 180 |
| agctggttga | agaagagctg | gaccgtgctc | aggagcgcct | ggccactgcc | ctgcaaaagc | 240 |
| tggaagaagc | tgaaaaagct | gctgatgaga | gtgagagagg | tatgaaggtt | attgaaaacc | 300 |
| gggccttaaa | agatgaagaa | aagatggaac | tccaggaaat | ccaactcaaa | gaagctaagc | 360 |
| acattgcaga | agaggcagat | aggaagtatg | aagaggtggc | tcgtaagttg | gtgatcattg | 420 |
| aaggagactt | ggaacgcaca | gaggaacgag | ctgagctggc | agagtcccgt | gccgagaga | 480 |
| tggatgagca | gattagactg | atggaccaga | acctgaagtg | tctgagtgct | gctgaagaaa | 540 |
| agtactctca | aaaagaagat | aaatatgagg | aagaaatcaa | gattcttact | gataaactca | 600 |
| aggaggcaga | gacccgtgct | gagtttgctg | agagatcggt | agccaagctg | gaaaagacaa | 660 |
| ttgatgacct | ggaagagcgt | ctctacagcc | aacttgagcg | aaaccgcctg | ctttctaatg | 720 |
| agctgaagct | aacgctgcat | gatctgtgtg | actgatgggc | agggctcaat | gatgcccatt | 780 |
| aaactgagct | tactgctcac | accactgacc | tggaccccaa | caaaaagctg | attgtctttt | 840 |
| taaaagttat | tattttagcc | ctgagcaaat | tgcattttaa | ttggggcagt | tagaatgttg | 900 |
| atttcctaac | agcattgtga | agttgaccat | tgtgaagttt | ctgtccttta | aagagatta | 960 |
| tgggtgaaga | agggagggc | ctgagagatt | atagtgagaa | aacttgcgag | aattttgttt | 1020 |
| tccacccta | tttgctgctc | tttcacttgg | gcactgactg | taggatatgt | tcccttgcat | 1080 |
| ggatgttttt | aacaataaaa | ggactgactt | gaaaaaaaaa | aaaaaaaaa | a | 1131 |

<210> SEQ ID NO 2
<211> LENGTH: 247
<212> TYPE: PRT
<213> ORGANISM: Homo sapiens

<400> SEQUENCE: 2

Met Ala Gly Ile Thr Thr Ile Glu Ala Val Lys Arg Lys Ile Gln Val
1               5                   10                  15

Leu Gln Gln Gln Ala Asp Asp Ala Glu Glu Arg Ala Glu Arg Leu Gln
            20                  25                  30

Arg Glu Val Glu Gly Glu Arg Arg Ala Arg Glu Gln Ala Glu Ala Glu
        35                  40                  45

Val Ala Ser Leu Asn Arg Arg Ile Gln Leu Val Glu Glu Glu Leu Asp
    50                  55                  60

Arg Ala Gln Glu Arg Leu Ala Thr Ala Leu Gln Lys Leu Glu Glu Ala
65                  70                  75                  80

Glu Lys Ala Ala Asp Glu Ser Glu Arg Gly Met Lys Val Ile Glu Asn
                85                  90                  95

Arg Ala Leu Lys Asp Glu Glu Lys Met Glu Leu Gln Glu Ile Gln Leu
            100                 105                 110

Lys Glu Ala Lys His Ile Ala Glu Glu Ala Asp Arg Lys Tyr Glu Glu
        115                 120                 125

```
Val Ala Arg Lys Leu Val Ile Ile Glu Gly Asp Leu Glu Arg Thr Glu
    130                 135             140
Glu Arg Ala Glu Leu Ala Glu Ser Arg Cys Arg Glu Met Asp Glu Gln
145                 150                 155                 160
Ile Arg Leu Met Asp Gln Asn Leu Lys Cys Leu Ser Ala Ala Glu Glu
                165                 170                 175
Lys Tyr Ser Gln Lys Glu Asp Lys Tyr Glu Glu Glu Ile Lys Ile Leu
            180                 185                 190
Thr Asp Lys Leu Lys Glu Ala Glu Thr Arg Ala Glu Phe Ala Glu Arg
        195                 200                 205
Ser Val Ala Lys Leu Glu Lys Thr Ile Asp Asp Leu Glu Glu Arg Leu
    210                 215                 220
Tyr Ser Gln Leu Glu Arg Asn Arg Leu Leu Ser Asn Glu Leu Lys Leu
225                 230                 235                 240
Thr Leu His Asp Leu Cys Asp
                245
```